United States Patent [19]

Berris

[11] Patent Number: 5,089,648
[45] Date of Patent: Feb. 18, 1992

[54] METHOD OF PRODUCING POLYSILANE COMPOUNDS

[75] Inventor: Bruce C. Berris, Baton Rouge, La.

[73] Assignee: Ethyl Corporation, Richmond, Va.

[21] Appl. No.: 577,280

[22] Filed: Sep. 4, 1990

[51] Int. Cl.$^5$ .................................................. C07F 7/08
[52] U.S. Cl. ............................................. 556/430; 556/406
[58] Field of Search ..................................... 556/430, 406

[56] References Cited

U.S. PATENT DOCUMENTS

| | | | |
|---|---|---|---|
| 3,631,195 | 12/1971 | Frey et al. | 556/406 |
| 3,631,197 | 12/1971 | Klosowski et al. | 556/406 |
| 4,578,495 | 3/1986 | Soula et al. | 556/430 X |
| 4,590,253 | 5/1986 | Hasegawa et al. | 556/430 |
| 4,808,685 | 2/1989 | Bortolin | 556/430 X |
| 4,973,723 | 11/1990 | Cawthon et al. | 556/406 |

FOREIGN PATENT DOCUMENTS 0238826  9/1987  European Pat. Off. ............ 556/430

*Primary Examiner*—Paul F. Shaver
*Attorney, Agent, or Firm*—Terry B. Morris; Steven R. Eck

[57] ABSTRACT

Improved methods for producing polysilane compounds using tetrakis(triethylphosphine)nickel (O) catalysts.

14 Claims, No Drawings

METHOD OF PRODUCING POLYSILANE COMPOUNDS

BACKGROUND

Polysilane compounds have been produced heretofore by the reaction of dichlorosilane with metallic sodium. In these processes the silane has two R groups wherein R each represents hydrogen or hydrocarbon group, but not both R's are hydrogen at the same time. However, the method disadvantageously needs two moles of metallic sodium per mole of monomeric silane compound, and the use of metallic sodium in large amounts may not be feasible in the industrial production of polysilane compounds since, for example, sodium is readily combustible. Also, sodium tends to agglomerate during reactions, which can cause agitators to bind. The variability of sodium agglomerate size is difficult to control, causing product quality problems. Moreover, the thus produced polysilane compound tends to contain residual chloride ions which adversely affect the electrochemical properties of the polymer.

J. Am. Chem. Soc., 108, 4059 (1986) proposed a method in which a phenylsilane is polymerized in the presence of an organotitanium complex to produce an $(RSiH_2)_m(RSiH)_n$ compound wherein n is about six and m is 0 or 2.

J. Organometal Chem., 55 (1973), C7-C8, described the heating of a monomeric hydrosilane compound in the presence of an organorhodium complex, $(Ph_3P)_3RhCl$, which provides oligomers such as dimers or trimers of the hydrosilane together with a significant amount of disproportionation product. The disproportion product contaminates the desired polysilane compound and can not be readily removed from the polysilane compound.

U.S. Pat. No. 4,900,861 describes organocomplexes of nickel, cobalt, ruthenium, palladium and iridium effective as catalysts for the polymerization of a monomeric silane compound to produce higher molecular weight polysilane compound with substantially no by-products of undesired disproportionation products.

There remains a need for improved methods of polymerizing silane and polysilane precursive material to produce polysilane compounds.

SUMMARY

This invention relates to methods of producing polysilane compounds by the polymerization of monomeric or oligomeric silane precusor material in the presence of nickel phosphine catalysts.

Improved methods have now been discovered for producing polysilane compounds. These methods include the use of tetrakis-(triethylphosphine)nickel(O) catalysts. The catalysts used provide increased activity requiring less catalyst. Additionally, they provide faster reactions.

DESCRIPTION OF THE PREFERRED EMBODIMENTS

In one embodiment the present invention is a method for polymerizing a monomeric or oligomeric silane precursor material to produce a polysilane compound. This method comprises polymerizing an appropriate monomeric or oligomeric silane precursor material in the presence of an effective amount of a tetrakis(triethylphosphine)nickel(O) catalyst producing a polysilane compound having an average molecular weight of about 500 or more. Unexpectedly the character of the tetrakis-(triethyl phosphorous) nickel(o) catalyst provides enhanced activity and produces larger silane oligomers than previously attained.

The nickel catalysts used in the present invention are tetrakis(triethylphosphine)nickel(O) compounds. These compounds are composed with three ethyl groups attached to the four phosphorous atoms attached to the nickel atom and can be represented by the following formula:

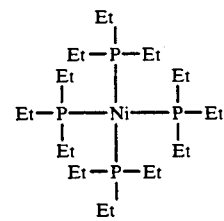

where Et is ethyl, P is phosphorous and Ni is nickel. Hereinafter, this catalyst will alternatively be named "tep Ni".

This catalyst (tep Ni) and its production are reported widely in the literature, as in U.S. Pat. No. 3,907,850 and 3,152,158, incorporated herein in their entirety by reference.

The tep Ni catalyst structure can have a large increase in activity on a weight basis over other known catalysts such as monomeric $(Ph_3P)_2Ni(CO)_2$ and $Ni(Ph_3P)_4$ (where Ph is phenyl, P is phosphorous and Ni is nickel). The preferred catalyst can produce a nearly quantitative yield of products with molecular weights of about 500 or more, preferably in the range of about 1000 to about 2000. Induction periods were relatively short, with accompanying gas evolution immediately observable.

In accordance with the invention, there is provided a method of producing a polysilane compound which comprises polymerizing a monomeric silane precursor compound represented by the general formula

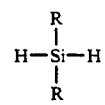

wherein R independently represents hydrogen or hydrocarbon group, but not both R's are hydrogen at the same time. When only one R is hydrogen, the compound can be represented by the formula $RSiH_3$, wherein R is an alkyl, aryl or alkylaryl group, as described hereinafter.

Alternatively, an oligomeric compound can be used instead of the monomeric silane. The oligomeric silane compound used in the invention can be a polymeric silane precursor material, e.g. a silane polymer, which by example can be represented by the general formula

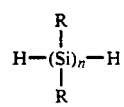

wherein R independently represents hydrogen or a hydrocarbon group, but not both R's are hydrogen at the same time, and n can range from about 2 to about 10.

These precursor materials can be linear, branched or cyclic.

The R group for either monomeric or oligomeric silane units is a hydrocarbon group such that the silane unit is preferably either alkylsilane, arylsilane, dialkylsilane, diarylsilane or alkylarylsilane, in which the alkyl group is either saturated or unsaturated and is preferably of one to about ten carbons, and the aryl group is either saturated or unsaturated and is preferably of about six to about fourteen carbons. The R group can be linear, branched or cyclic $C_2$ through $C_{20}$'s and higher in structure, or a combination of such characters.

Thus, the monomeric silane compound used in the invention can be exemplified by alkylsilanes such as methylsilane, ethylsilane, n-propylsilane, isopropylsilane, n-butylsilane, t-butylsilane, sec-butylsilane, n-pentylsilane, n-hexylsilane or n-heptylsilane; aryl silanes such as phenylsilane, benzylsilane or phenethylsilane; dialkylsilanes such as dimethylsilane, methylethylsilane, diethylsilane, methyl-n-propylsilane, methylisopropylsilane, ethyl-n-propylsilane, ethylisopropylsilane, diisopropylsilane, di-n-butylsilane or di-n-pentylsilane; alkylarylsilanes such as methylphenylsilane, ethylphenylsilane; or diarylsilanes such as diphenylsilane, tolylsiane, xylylsiane, phenyl-o-tolylsilane, phenyl-p-tolylsilane, phenyl-m-tolylsilane, phenyl-p-chlorophenylsilane, phenyl-2,4-dimethylphenylsilane or phenyl-2,4-dichlorophenylsilane. Halophenyls (e.g. chlorophenyl or dichlorophenyl) are also included. The monomeric silane compound may be used singly or as a mixture of two or more of such monomeric silanes. Likewise, isomers are included, such as 2-methylphenylsilane and 4-methylphenylsilane for methylphenyl silane. Further, if desired, oligomers, preferably dimers or trimers, of the monomeric silane compounds may be used in place of the monomeric silanes or together therewith.

The preferred monomeric silane compound used in the invention is phenylsilane, methylphenylsilane, diphenylsilane, ethylphenylsilane, hexylsilane or butylsilane with phenylsilane, methylphenylsilane, diphenylsilane, hexylsilane and butylsilane most preferred These characterizations of the R groups for the silane units apply to both reactants and product silanes.

The product formed using either a monomeric or oligomeric silane precursor material can be either a linear, branched, cyclic or bicyclic polysilane. There need not be the same character of being linear, branched or cyclic for the precursive material as there is in the product, but there can be. The product produced can typically have an average molecular weight of about 500 or more.

One set of products produced by the present invention are linear structure polysilane compounds. The linear structure polysilane compound may be represented by

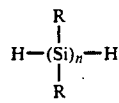

wherein R is the same as before, and n is an integer of not less than two, usually in the range of from two to about twenty. Preferably, n has a value of at least about ten.

Branched structure polysilane compounds can also be produced. For instance, disubstituted silanes can be reacted to produce dehydrodimers As an example, when disubstituted silanes diethylsilanes or diphenylsilanes are reacted in the presence of tep Ni, the respective products are the dehydrodimers 1,1,2,2-tetraethyldisilanes or 1,1,2,2- tetraphenyldisilanes.

The branched structure polysilane compounds have a silane branch through a Si-Si bond. An exemplified polysilane compound of the branched structure may be as follows:

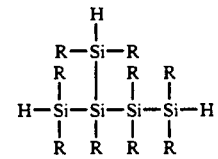

In addition to the linear or branched polysilanes, cyclic polysilanes can be produced. The cyclic structure polysilane compounds are represented by:

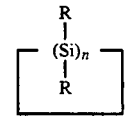

wherein R and n (at least 3) are as previously described. Bicyclic products with about 7 to about 8 silicon atoms can also be produced, e.g. octaalkylbicyclo[2.2.2]octasilaoctane and/or heptaalkylbicyclo[2.2.1]heptasilaheptane.

In the method of the invention, the polymerization of the monomeric silane compound is carried out usually at temperatures in the range of from about −20 C. to about 120° C., preferably from about 20° C. to about 50° C. The reaction time may be in the range of from about 10 minutes to about 5 days or longer. The reaction time is preferably from about 1 hour to 1 day. These reaction times depend upon the reaction temperature employed. The higher the temperature, the less reaction time is required.

Usually the reaction is carried out in the absence of a solvent(eg. "neat"), but may be carried out in the presence of solvent, preferably inert to the reactants. The solvents include, for example, aromatic hydrocarbons such as benzene or toluene, ethers such as methyl ethyl ether, diethyl ether, tetrahydrofuran or dioxane, acid amides such as dimethylformamide, or acid esters such as ethyl acetate or butyl acetate.

The amount of catalyst employed in the reaction is usually from about 0.0001 mole to about 0.5 moles, preferably from about 0.001 moles to about 0.05 moles, per mole of the monomeric or oligomeric silane compound used.

It is desired that the reaction be carried out under an inert gas atmosphere such as nitrogen or argon. The progress of the reaction is confirmed by evolution of hydrogen gas from the reaction mixture.

According to the invention, the monomeric silane compound polymerizes readily in the presence of the catalyst to provide polysilane compounds in high yields with substantially no by-production of undesired disproportionation products. The catalyst used may be recovered from the reaction mixture, if desired.

The invention will now be described with reference to experimental examples which are, however, illustrative only and the invention is not limited to the examples.

EXAMPLE 1

Polymerization of n-butylsilane with Ni(PEt$_3$)$_4$

A mixture of n-butylsilane (0.578 g) and Ni(PEt3)4 (10 mg) was stirred in an open vial in an argon atmosphere. Gas evolution was immediately observed. After four hours the reaction had almost stopped. A sample of the reaction mixture was analyzed by GC-MS (30m DB5 column, 150° to 300° C., 10° C. per min) giving the following results:

| Component | Retention Time | Area % |
|---|---|---|
| Monosilane | 1:20 | 6 |
| Disilane | 1:48 | 6 |
| Trisilane (linear) | 4:13 | 24 |
| Tetrasilane (linear) | 7:31 | 2 |
| Tetrasilane (linear) | 8:00 | 32 |
| Pentasilane (linear) | 11:00 | 4 |
| Pentasilane (linear) | 11:20 | .13 |
| Pentasilane (cyclic) | 11:53 | 1 |
| Pentasilane (cyclic) | 12:02 | 1 |
| Hexasilane (linear) | 14:12 | 2 |
| Hexasilane (linear) | 14:28 | 3 |
| Hexasilane (cyclic) | 14:50 | 1 |
| Heptasilane (linear) | 17:06 | <1 |
| Heptasilane (linear) | 17:28 | <1 |
| Heptasilane (cyclic) | 17:41 | <1 |
| Heptasilane (cyclic) | 17:54 | <1 |
| Heptasilane (cyclic) | 18:04 | <1 |
| Heptasilane (cyclic) | 18:11 | <1 |

A repetition in the component column indicates that diastereomers have been separated.

EXAMPLES 2 THROUGH 9

Polymerization of n-hexylsilane with Ni(PEt$_3$)$_4$

A series of experiments were run using 10 mg of Ni(PEt$_3$)$_4$ and 1 g of hexylsilane. As indicated in the following table, in some runs 1 g of toluene was added, and a nitrogen purge through the solution was used in some runs. After 1-2 days, the product was analyzed by GPC and the weight-average molecular weight estimated by comparison with polyethylene glycol standards.

Polymerization of Hexylsilane Catalyzed by Ni(PEt$_3$)$_4$

| Exp. | Temp. | Purge | Solvent | M$_w$ |
|---|---|---|---|---|
| 2 | 25 | on | toluene | 869 |
| 3 | 100 | on | toluene | 726 |
| 4 | 25 | off | toluene | 989 |
| 5 | 100 | off | toluene | 750 |
| 6 | 25 | on | neat | 951 |
| 7 | 100 | on | neat | 910 |
| 8 | 25 | off | neat | 944 |
| 9 | 100 | off | neat | 861 |

EXAMPLES 1-13

Comparison of Catalysts

The following table provides the results of polymerizing the hexylsilane monomer using nickel. Each experiment was performed by stirring 10 to 20 milligrams of catalyst together with 1 gram of the silane monomer in an open vial under argon for one to two days (unless indicated otherwise) at room temperature. "Ph" represents a phenyl group.

| Exp. | Catalyst | Product | Molecular Weight |
|---|---|---|---|
| 10 | (Ph$_3$P)$_2$Ni(CO)$_2$ | no reaction | — |
| 11 | Ni(Ph$_3$P)$_4$ | slow reaction | — |
| 12 | Ni(Et$_3$P)$_4$-first day | polysilane | 950 |
| 13 | Ni(Et$_3$P)$_4$-fifth day | polysilane | 1450 |

What is claimed is:

1. A method for polymerizing a monomeric or oligomeric silane precursor material to produce a polysilane compound comprising polymerizing said monomeric or oligomeric silane precursor material in the presence of an effective amount of a tetrakis(triethylphosphine)-nickel(O) catalyst for producing an average molecular weight of about 500 or more for said polysilane compound.

2. The method of claim 1 wherein the silane precursor is RSiH$_3$ and R is an alkyl, aryl, or alkylaryl group.

3. The method of claim 2 wherein said RSiH$_3$ is phenyl silane, phenylalkyl silane, alkylphenyl silane or halophenyl silane.

4. The method of claim 2 wherein said alkylsilane has from one to about ten carbon atoms.

5. The method of claim 4 wherein the alkyl group of the alkylsilane is a linear alkyl group.

6. The method of claim 5 wherein the linear alkyl group is a methyl, ethyl or n-propyl group.

7. The method of claim 2 wherein R of RSiH$_3$ is a phenyl or methylphenyl group.

8. The method of claim 1 wherein the monomeric silane precursor is R$_2$SiH$_2$, each R is independently either an alkyl, aryl or alkylaryl group, and the product is a dehydrodimer.

9. The method of claim 1 wherein said polysilane compound is linear.

10. The method of claim 1 wherein said polysilane compound has from about two to about twenty silicon atoms.

11. The method of claim 1 wherein said polysilane compound has at least ten silicon atoms.

12. The method of claim 11 wherein said average molecular weight is from at least about 1000 to about 2000.

13. The method of claim 1 wherein said polymerization is performed in a solvent.

14. The method of claim 13 wherein the solvent is toluene.

* * * * *